(12) United States Patent
Italiaie et al.

(10) Patent No.: US 11,284,924 B1
(45) Date of Patent: Mar. 29, 2022

(54) ADJUSTABLE SPINAL IMPLANT, SYSTEM AND METHOD

(71) Applicant: Warsaw Orthopedic, Inc., Warsaw, IN (US)

(72) Inventors: Christel Italiaie, Memphis, TN (US); Leigh A. Folger, Memphis, TN (US)

(73) Assignee: WARSAW ORTHOPEDIC, INC, Warsaw, IN (US)

( * ) Notice: Subject to any disclaimer, the term of this patent is extended or adjusted under 35 U.S.C. 154(b) by 0 days.

(21) Appl. No.: 17/123,912

(22) Filed: Dec. 16, 2020

(51) Int. Cl.
A61B 17/70 (2006.01)

(52) U.S. Cl.
CPC ...... A61B 17/7052 (2013.01); A61B 17/7011 (2013.01)

(58) Field of Classification Search
CPC ............ A61B 17/7052; A61B 17/7043; A61B 17/7049; A61B 17/7041; A61B 17/705
See application file for complete search history.

(56) References Cited

U.S. PATENT DOCUMENTS

| | | | |
|---|---|---|---|
| 6,277,120 B1 | 8/2001 | Lawson | |
| 7,166,108 B2 | 1/2007 | Mazda et al. | |
| 7,481,828 B2 | 1/2009 | Mazda et al. | |
| 7,572,277 B2 | 8/2009 | Roussouly et al. | |
| 7,655,025 B2 | 2/2010 | Ritland | |
| 7,717,938 B2 | 5/2010 | Kim et al. | |
| 7,803,174 B2 | 9/2010 | Denis et al. | |
| 7,806,912 B2 | 10/2010 | Lawton et al. | |
| 7,867,255 B2 | 1/2011 | Miller et al. | |
| 7,942,901 B2 | 5/2011 | Rezach | |
| 7,959,654 B2 | 6/2011 | Mazda et al. | |
| 8,021,399 B2 | 9/2011 | Ritland | |
| 8,162,946 B2 | 4/2012 | Baccelli et al. | |
| 8,172,843 B2 | 5/2012 | Baccelli et al. | |
| 8,236,028 B2 | 8/2012 | Kalfas et al. | |
| 8,246,657 B1 | 8/2012 | Samuel | |
| 8,298,269 B2 | 10/2012 | Null et al. | |
| 8,323,319 B2 | 12/2012 | Mazda et al. | |
| 8,372,119 B2 | 2/2013 | Kim et al. | |
| 8,430,916 B1 | 4/2013 | Winslow et al. | |
| 8,430,918 B2 | 4/2013 | Baccelli et al. | |
| 8,715,323 B2 | 5/2014 | Ballard et al. | |
| 8,852,237 B2 | 10/2014 | Kalfas et al. | |
| 8,870,870 B2 | 10/2014 | Baccelli et al. | |
| 8,926,668 B2 | 1/2015 | Douget | |

(Continued)

Primary Examiner — Julianna N Harvey
(74) Attorney, Agent, or Firm — Fox Rothschild LLP

(57) ABSTRACT

A spinal construct is disclosed. The spinal construct may include a connector having a body including a first implant cavity and a second implant cavity. The first implant cavity being defined, at least partly, by at least two threaded arm portions. The first implant cavity may include a first receiving cavity configured to adjustably orient a first rod in a plane substantially perpendicular to the first axis. The second implant cavity may include a second receiving cavity configured to orient a second rod. In some embodiments, the threaded arm portions may be configured to receive a first set screw such that when the first set screw is fully tightened along the first axis the first rod is fixed relative to the body in a direction extending substantially parallel with the plane. In some embodiments, the body may further include a threaded opening communicating with the second receiving cavity.

18 Claims, 8 Drawing Sheets

(56) References Cited

U.S. PATENT DOCUMENTS

| | | |
|---|---|---|
| 8,936,625 B2 | 1/2015 | Larroque-Lahitette et al. |
| 8,940,020 B2 | 1/2015 | Rathbun |
| 8,961,572 B2 | 2/2015 | Kim et al. |
| 8,992,575 B1 * | 3/2015 | Di Lauro ............ A61B 17/7037 606/253 |
| 8,998,957 B2 | 4/2015 | Kalfas et al. |
| 8,998,961 B1 | 4/2015 | Ziemek et al. |
| 9,492,205 B2 | 11/2016 | Alsup et al. |
| 9,918,748 B2 | 3/2018 | Kalfas et al. |
| 9,980,755 B2 | 5/2018 | Murray et al. |
| 10,238,432 B2 | 3/2019 | Carruth et al. |
| 10,251,678 B2 | 4/2019 | Alsup et al. |
| 10,383,663 B2 | 8/2019 | Murray et al. |
| 2003/0093078 A1 * | 5/2003 | Ritland ............ A61B 17/7025 606/900 |
| 2005/0131404 A1 | 6/2005 | Mazda et al. |
| 2005/0171537 A1 | 8/2005 | Mazel et al. |
| 2006/0079892 A1 | 4/2006 | Roychowdhury et al. |
| 2007/0270817 A1 | 11/2007 | Rezach |
| 2008/0109039 A1 * | 5/2008 | Michielli ............ A61B 17/7049 606/251 |
| 2008/0140124 A1 | 6/2008 | Jeon et al. |
| 2009/0228046 A1 | 9/2009 | Garamszegi |
| 2010/0249845 A1 | 9/2010 | Meunier et al. |
| 2010/0280552 A1 | 11/2010 | Lee |
| 2011/0301644 A1 | 12/2011 | Belliard |
| 2012/0029571 A1 | 2/2012 | Schwab et al. |
| 2012/0158064 A1 | 6/2012 | Kroll |
| 2012/0271354 A1 | 10/2012 | Baccelli et al. |
| 2012/0303121 A1 | 11/2012 | Douget et al. |
| 2014/0094850 A1 | 4/2014 | Clement et al. |
| 2014/0336706 A1 | 11/2014 | Garamszegi |
| 2016/0166289 A1 * | 6/2016 | Alsup ................ A61B 17/705 606/253 |
| 2017/0281237 A1 | 10/2017 | Murray et al. |
| 2017/0281243 A1 * | 10/2017 | Murray ............ A61B 17/7004 |
| 2017/0281246 A1 | 10/2017 | Murray et al. |
| 2018/0098798 A1 | 4/2018 | Italiaie et al. |
| 2018/0125538 A1 | 5/2018 | Daniels et al. |
| 2018/0280062 A1 | 10/2018 | Lee et al. |
| 2018/0280063 A1 | 10/2018 | Lee et al. |
| 2019/0175226 A1 | 6/2019 | Carruth et al. |
| 2019/0321083 A1 | 10/2019 | Murray et al. |

* cited by examiner

ADJUSTABLE SPINAL IMPLANT, SYSTEM AND METHOD

CROSS-REFERENCE TO RELATED U.S. PATENT APPLICATION

This Application hereby incorporates the disclosure of U.S. patent application Ser. No. 16/395,498, titled SPINAL IMPLANT SYSTEM AND METHOD, filed Apr. 26, 2019, into this document by reference in its entirety.

TECHNICAL FIELD

The present disclosure generally relates to medical devices for the treatment of musculoskeletal disorders, and more particularly to a spinal implant system and a method for treating a spine.

BACKGROUND

Spinal pathologies and disorders such as scoliosis, kyphosis, and other curvature abnormalities, degenerative disc disease, disc herniation, osteoporosis, spondylolisthesis, stenosis, tumor and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs including vertebral rods are often used to provide stability to a treated region. Rods redirect stresses away from a damaged or defective region while healing takes place to restore proper alignment and generally support vertebral members. During surgical treatment, one or more rods and bone fasteners can be delivered to a surgical site. The rods may be attached via the fasteners to the exterior of two or more vertebral members.

Conventional surgery may often involve a plurality of connectors that are attached to corresponding pedicle screws in a series of vertebrae. Conventional connectors are only capable of fixing the rod in a single orientation and do not allow the rod to pivot. That is to say, the rod, connector, and pedicle screw fix the rod system in a single extension direction. In some initial surgeries, and in some revision surgeries, a fixed system is disadvantageous because a fixed system may not provide a surgeon and/or patient with sufficient range of motion to obtain a target alignment.

SUMMARY

In one aspect, a spinal construct is disclosed. The spinal construct may include a connector having a body including a first implant cavity and a second implant cavity. The first implant cavity may be defined, at least partly, by at least two threaded arm portions defining a first axis between the at least two threaded arm portions. Additionally, the first implant cavity may include a first receiving cavity configured to adjustably orient a first rod in a plane substantially perpendicular to the first axis, and the second implant cavity may include a second receiving cavity configured to orient a second rod. In some embodiments, the threaded arm portions may be configured to receive a first set screw such that when the first set screw is fully tightened along the first axis the first rod is fixed relative to the body in a direction extending substantially parallel with the plane. In some embodiments, the body further includes a threaded opening communicating with the second receiving cavity, the threaded opening defining a second axis and being configured to receive a second set screw such that when the second set screw is fully tightened the second rod may be fixed relative to the body.

In another aspect, the first axis and the second axis may extend in different directions, and the first rod and the second rod may extend in different directions.

In another aspect, the first axis and the second axis may be disposed in a non-perpendicular orientation relative to one another, and the first rod and the second rod may extend in a non-perpendicular orientation relative to one another.

In another aspect, the first receiving cavity may include an arcuate rail extending along a bottom surface, the arcuate rail being defined, at least partly, by a segment of a circle having a radius that corresponds to an external radius of the first rod. Additionally, the arcuate rail may be configured to facilitate pivoting of the first rod in the plane.

In another aspect, the first receiving cavity may include a first enlarged portion and a second enlarged portion opposite the first enlarged portion, and the first and second enlarged portions may define the extent the first rod may be adjustably oriented in the plane.

In another aspect, the first receiving cavity may include an internal passageway having an arcuate rail extending along a bottom surface. The arcuate rail may be defined, at least partly, by a segment of a circle having an internal radius that corresponds to an external radius of the first rod. The internal passageway may further include a first enlarged portion and a second enlarged portion symmetrically disposed on opposite sides of the arcuate rail. In some embodiments, a radius of the internal passageway gradually increases from the arcuate rail to an outermost edge of the first enlarged portion, and a radius of the internal passageway gradually increases from the arcuate rail to an outermost edge of the second enlarged portion.

In another aspect, the arcuate rail may be configured to facilitate pivoting of the first rod in the plane, and the first and second outermost edge portions may define the extent the first rod may be adjustably oriented in the plane.

In another aspect, the first set screw may include at least one of the following: a plain cup screw head, a knurled cup screw head, a flat screw head, an oval screw head, a cone screw head, a half-dog screw head, and a soft tipped screw head.

In another aspect, the first set screw and the second set screw are different types of set screws.

In another aspect, at least one insert may be further included. The at least one insert may be inserted into a space between the first rod and at least one of the first enlarged portion and the second enlarged portion. Additionally, the insert may be configured to facilitate fixation of the first longitudinal member.

In another aspect, a spinal construct system is disclosed. The spinal construct system may include at least one anchoring member configured to couple to a corresponding pedicle screw. The system may further include a plurality of connectors, each connector including a corresponding body having a corresponding first implant cavity and a corresponding second implant cavity. Additionally, each first implant cavity may be defined, at least partly, by at least two corresponding threaded arm portions defining a corresponding first axis extending between the at least two corresponding threaded arm portions. Each first implant cavity may include a corresponding first receiving cavity configured to adjustably orient a first rod in a range of extension directions substantially perpendicular to the first axis. Each second implant cavity may include a corresponding second receiving cavity configured to orient a second rod. In some embodiments, each of the corresponding threaded arm portions may be configured to receive a corresponding first set screw such that when the corresponding first set screw is fully tightened along the first axis the first rod is fixed relative to the corresponding body in a direction comprising the range of extension directions. In some embodiments, each body further includes a corresponding threaded opening communicating with the corresponding second receiving cavity, each threaded opening defining a corresponding second axis and being configured to receive a corresponding second set screw such that when the corresponding second set screw is fully tightened the second rod is fixed relative to the corresponding body.

In another aspect, each first axis and each corresponding second axis may extend in different directions, and the first rod and the second rod may extend in different directions.

In another aspect, each first axis and each corresponding second axis may be disposed in a non-perpendicular orientation relative to one another, and the first rod and the second rod may extend in a non-perpendicular orientation relative to one another.

In another aspect, each first receiving cavity may include a corresponding arcuate rail extending along a corresponding bottom surface, each arcuate rail may be defined, at least partly, by a segment of a circle having a radius that corresponds to an external radius of the first rod, and each arcuate rail may be configured to facilitate pivoting of the first rod within the range of the extension directions.

In another aspect, each first receiving cavity may include a first enlarged portion and a second enlarged portion opposite the first enlarged portion, and each of the first and second enlarged portions may define the extent the first rod may be adjustably oriented within the range of the extension directions.

In another aspect, each first receiving cavity may include a corresponding internal passageway. Each internal passageway may include a corresponding arcuate rail extending along a corresponding bottom surface, the arcuate rail being defined, at least partly, by a segment of a circle having an internal radius that corresponds to an external radius of the first rod. Each internal passageway may further include a corresponding first enlarged portion and a corresponding second enlarged portion symmetrically disposed on opposite sides of the corresponding arcuate rail. In some embodiments, a radius of each corresponding internal passageway gradually increases from the corresponding arcuate rail to an outermost edge of the corresponding first enlarged portion, and a radius of each internal passageway gradually increases from the corresponding arcuate rail to an outermost edge of the corresponding second enlarged portion.

In another aspect, each arcuate rail may be configured to facilitate pivoting of the first rod within the range of the extension directions, and each of the first and second outermost edge portions may define the extent the first rod may be adjustably oriented within the range of the extension directions.

In another aspect, each first set screw may be and/or include at least one of the following: a plain cup screw head, a knurled cup screw head, a flat screw head, an oval screw head, a cone screw head, a half-dog screw head, and a soft tipped screw head.

In another aspect, each first set screw and each second set screw may be different types of set screws.

In another aspect, the system may further include at least one insert, the insert being inserted into a space between the first rod and at least one of the first enlarged portions and the second enlarged portions of at least one connector. In some embodiments, the insert is configured to facilitate fixation of the first longitudinal member.

BRIEF DESCRIPTION OF THE DRAWINGS

The present disclosure will become more readily apparent from the specific description accompanied by the following drawings, in which.

DETAILED DESCRIPTION

Figure 1:
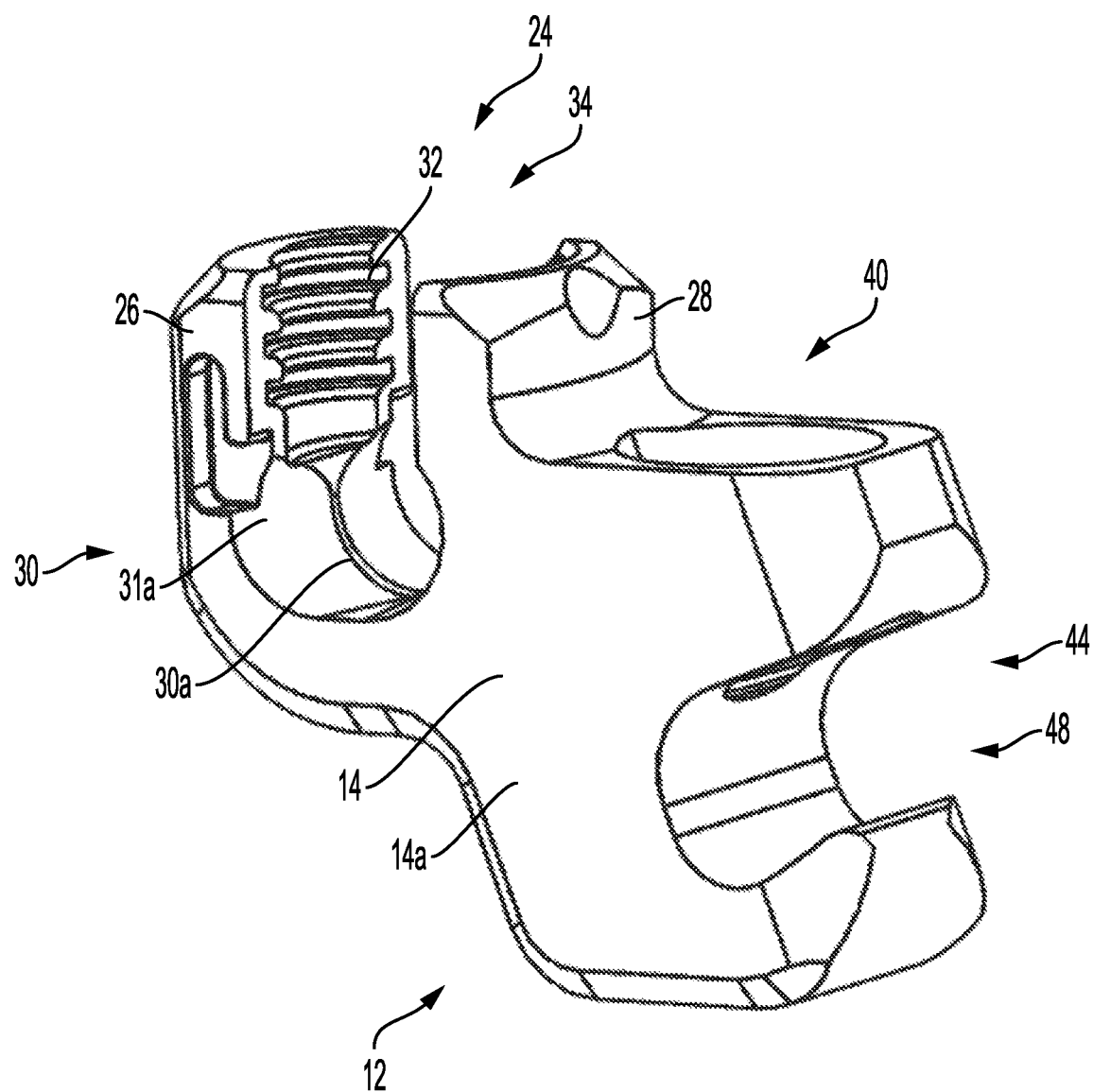
FIG. 1 is a perspective view of a spinal implant connector in accordance with the principles of the present disclosure.
Figure 2:
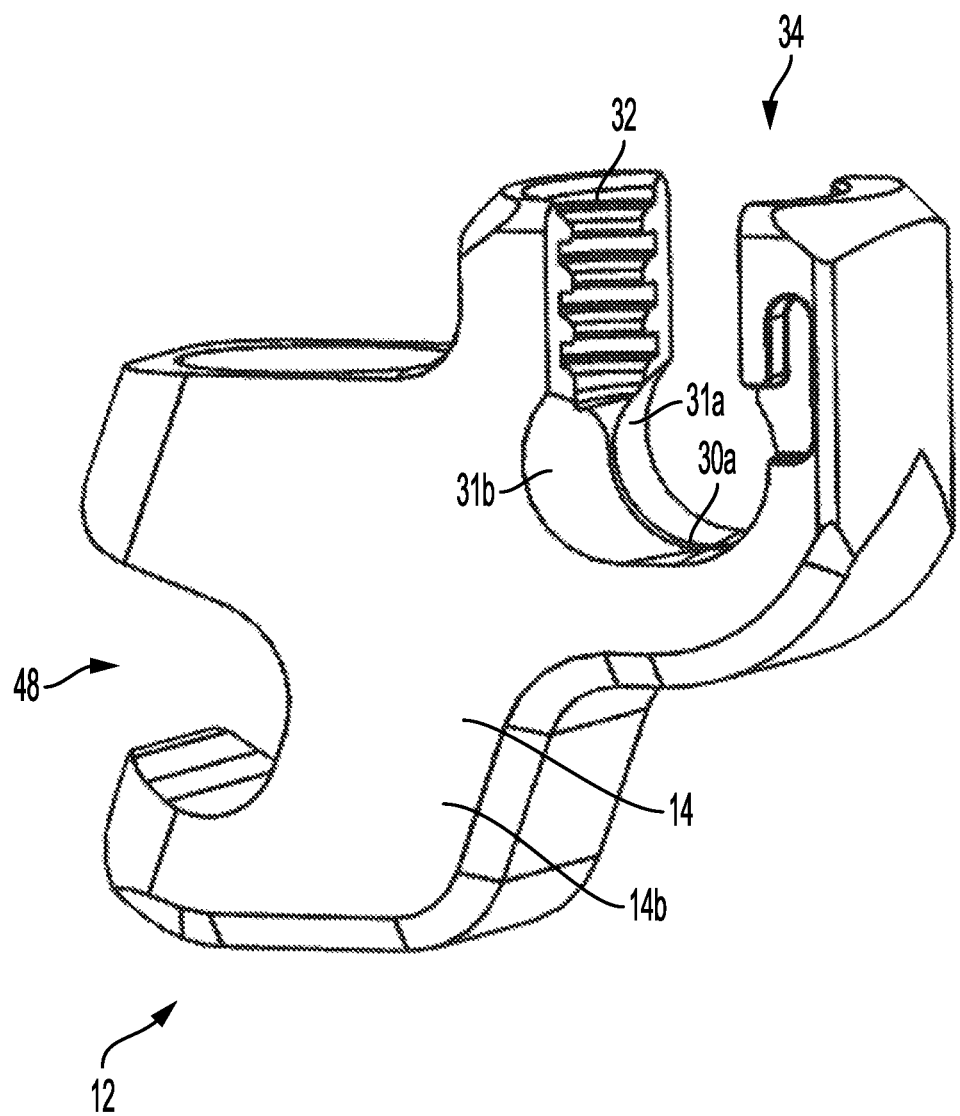
FIG. 2 is an alternate perspective view of a spinal implant connector in accordance with the principles of the present disclosure.

The exemplary embodiments of the surgical system and related methods of use disclosed are discussed in terms of medical devices for the treatment of musculo skeletal disorders and more particularly, in terms of a surgical system and method for treatment of a spine disorder. In some embodiments, the systems and methods of the present disclosure are employed with a spinal joint fusion, for example, with a cervical, thoracic, lumbar and/or sacral region of a spine.

In some embodiments, the systems and methods of the present disclosure are employed with a revision surgery to correct or otherwise assist with a previous surgery. At least one example previous surgery may include the installation of a plurality of pedicle screws in adjacent vertebrae of a patient's spine. Each of the plurality of pedicle screws may be coupled to a corresponding anchoring member configured to receive a longitudinal rod and orient the longitudinal rod in a direction corresponding to a target alignment of the patient's spine. Unfortunately, in some instances, the overall alignment of the longitudinal rod may have shifted away from the intended target alignment. Such shifting may occur to due to trauma to the patient's spine, aging of the patient, and/or mechanical failure of any of the previously installed parts. In these instances, the patient may undergo a revision procedure where a second set of pedicle screws may be installed in adjacent vertebrae of the patient's spine. For example, a second array of new pedicle screws may be installed in addition to the previously installed pedicle screws. The second set of pedicle screws may be coupled to a second set of anchoring members that are in turn coupled to a second longitudinal rod. In these revision surgeries, a connector may be used to connect the first longitudinal rod to the second longitudinal rod and thereby bring the alignment of the patient's spine back into the target alignment (or at least improve the patient's current spinal alignment). The present disclosure describes a spinal construct including a connector that enables the adjustment of the orientation of a longitudinal rod within a retaining portion of the connector. For example, spinal constructs and connectors in accordance with the present disclosure provide a means to fixedly attach a first longitudinal rod to a first retaining portion of a connector and place the second longitudinal rod in a second retaining portion of the connector where at least one of the longitudinal rods may be positioned in a range of orientations with respect to the connector. For example, an orientation or extension direction of the first longitudinal rod may be adjustable within a corresponding retaining portion of the connector. In this way, the present disclosure describes a connector having at least one retaining portion for receiving a rod that may fix the rod in a range of orientations with respect to the connector.

In some embodiments, the present surgical system includes a spinal construct having a connector. In some embodiments, the connector may include a tulip hybrid crosslink connector. In some embodiments, the connector includes a top loading spinal rod passageway and a side loading spinal rod passageway. The connector may be configured to connect a spinal rod with a spinal construct including, such as, for example, bone screws and a spinal rod. In some embodiments, the connector includes a first implant cavity and a second implant cavity. In some embodiments, at least one of the implant cavities is configured for side loading a spinal rod. In some embodiments, the connector includes an opening communicating with the first implant cavity and an opening communicating with the second implant cavity. In some embodiments, the first implant cavity may have a structural geometry facilitating the passive pivoting of a longitudinal rod. For example, the first implant cavity may define a passageway for receiving the rod that is enlarged on edge portions and/or fans out towards the edge portions thereby allowing the longitudinal rod to pivot laterally with respect to a center of the passageway.

In some embodiments, one or all of the components of the surgical system may be disposable, peel-pack, pre-packed sterile devices. One or all of the components of the system may be reusable. The system may be configured as a kit with multiple sized and configured components. For example, shims and inserts may also be provided for further facilitating the securement of the longitudinal rods. Similarly, various sized and types of set screws may be provided for various types and orientations of longitudinal rods.

In some embodiments, the surgical system of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the surgical system of the present disclosure may be employed with other osteal and bone related applications, including those associated with diagnostics and therapeutics. In some embodiments, the disclosed surgical system may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The surgical system of the present disclosure may also be alternatively employed with procedures for treating the lumbar, cervical, thoracic, sacral and pelvic regions of a spinal column. The surgical system of the present disclosure may also be used on animals, bone models and other non-living substrates, such as, for example, in training, testing and demonstration.

The surgical system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. In some embodiments, as used in the specification and including the appended claims, the term "tissue" includes soft tissue, ligaments, tendons, cartilage and/or bone unless specifically referred to otherwise.

The following discussion includes a description of a surgical system including a spinal construct, related components and methods of employing the surgical system in accordance with the principles of the present disclosure. Alternate embodiments are also disclosed. Reference is made in detail to the exemplary embodiments of the present disclosure, which are illustrated in the accompanying figures.

Referring generally to FIGS. 1-5B, there are illustrated components of a spinal implant connector 12. Referring generally to FIGS. 6A-7, there are illustrated components of a similar spinal implant connector 12a. The connectors 12 and 12a may be used as part of a surgical system, such as, for example, a spinal implant system 10 illustrated in FIG. 8.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, aluminum, commercially pure titanium, titanium alloys, Grade 5 titanium, superelastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tricalcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 comprises a spinal construct including a spinal implant connector 12. In some embodiments, connector 12 is configured to connect a first longitudinal rod 150 with bone screws 160 and a second longitudinal rod 152, (see FIG. 8). In some embodiments, the orientation of first longitudinal rod 150 may be adjustable, at least partly, and with respect to connector 12. In some embodiments, the first longitudinal rod 150 may be passively adjustable, e.g., the longitudinal rod may be adjustable within a corresponding passageway that is not necessarily mechanically adjusted by a rotatable member or the like.

Figure 8:
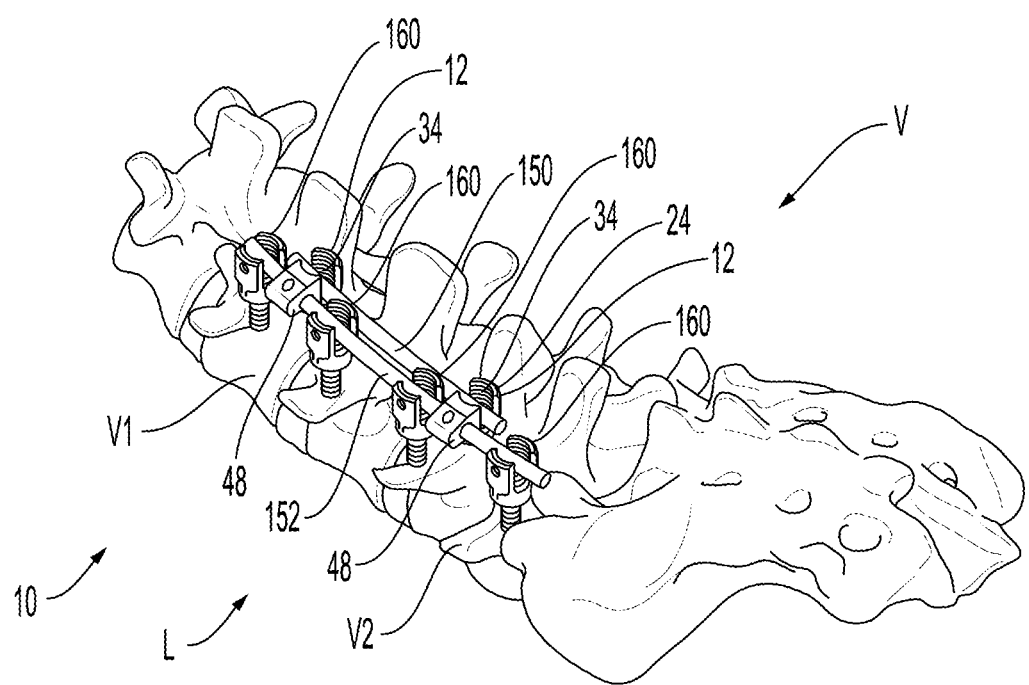
FIG. 8 is a perspective view of a spinal implant system including a plurality of spinal implant connectors in accordance with the principles of the present disclosure.

Connector 12 may include a body 14, e.g., a unitary body or a multicomponent body. In at least one embodiment, body 14 is formed of a single component material that is machined to include various contours, structural features, relationships, and/or functional geometry. Body 14 may include a first lateral surface 14a and a second lateral surface 14b opposite first lateral surface 14a. Body 14 may include a first implant cavity including a pair of spaced-apart arms 26, 28 that define, for example, a first receiving cavity 30 therebetween. In the illustrated embodiment, first receiving cavity 30 is configured for top loading of a spinal implant, such as, for example, first longitudinal rod 150, as shown in FIG. 8. However, in other embodiments, first receiving cavity 30 may be alternatively configured for side loading of a spinal implant.

Figure 5B:
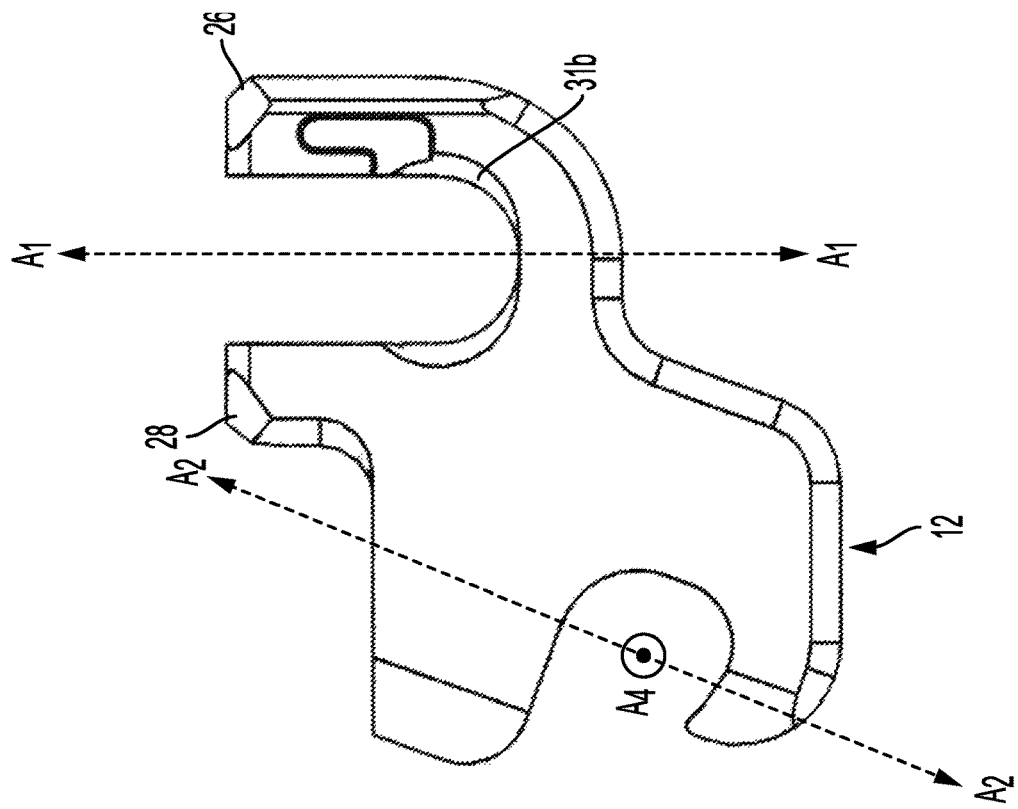
FIG. 5B is a side view of a spinal implant connector in accordance with the principles of the present disclosure.
Figure 5A:
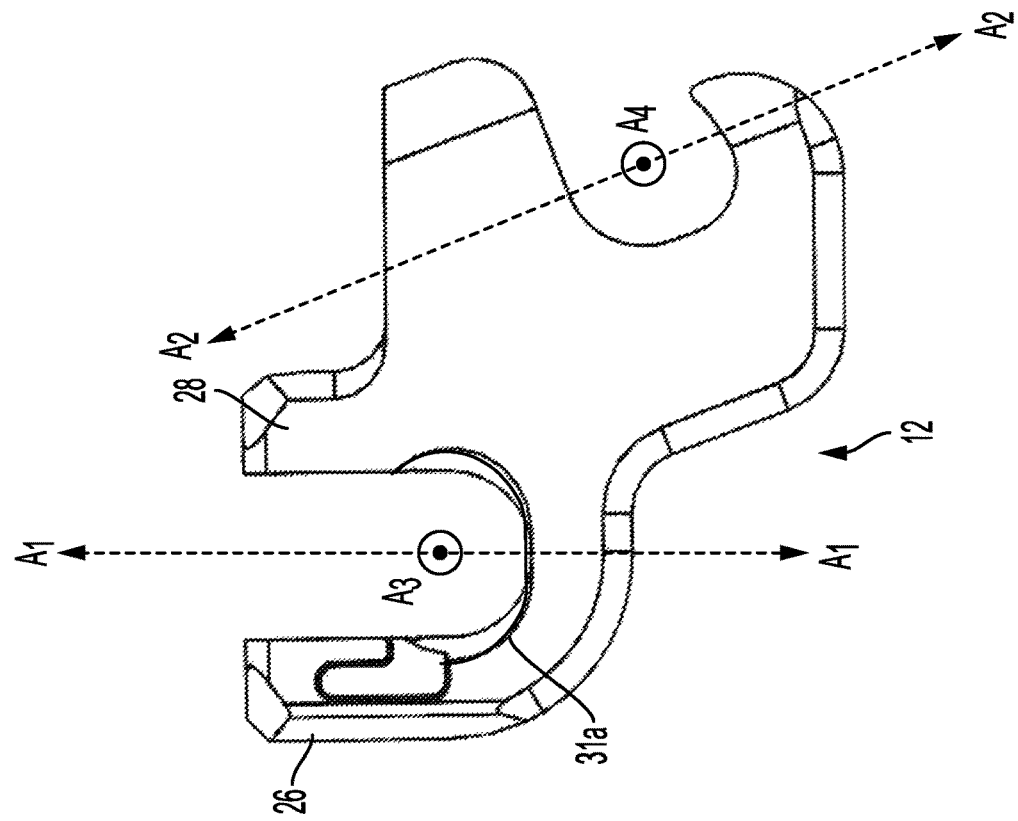
FIG. 5A is a side view of a spinal implant connector in accordance with the principles of the present disclosure.
Figure 6A:
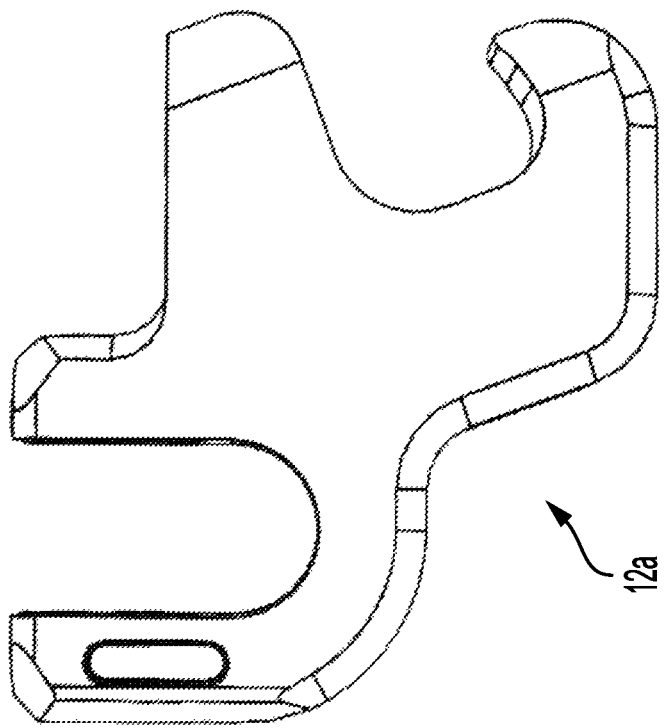
FIG. 6A is a side view of a spinal implant connector in accordance with the principles of the present disclosure.

Arms 26, 28 may each be threaded on an interior surface and extend parallel to axis A1, as shown in FIGS. 5A-5B. In some embodiments, arm 26 and/or arm 28 may be disposed at alternative orientations relative to axis A1, such as, for example, transverse and/or other angular orientations such as acute or obtuse, coaxial and/or may be offset or staggered. Arms 26, 28 may each include an arcuate outer surface extending between a pair of side surfaces of first and second lateral surfaces 14a, 14b. In some embodiments, at least one of the outer surfaces and the side surfaces of arms 26, 28 have at least one recess or cavity therein configured to receive an insertion tool, compression instrument and/or instruments for manipulating connector 12.

First receiving cavity 30 may comprise a first passageway for receiving a first longitudinal rod 150. In the illustrated embodiment, first receiving cavity 30 may be configured to adjustably orient a first longitudinal rod 150 in a plane substantially perpendicular to the first axis A1. For example, first longitudinal rod 150 may freely pivot and/or adjustably rotate laterally within first receiving cavity 30 in a direction and/or plane that is substantially perpendicular to the first axis A1. For example, first longitudinal rod 150 may project and/or extend away from lateral surfaces 14a, 14b. In some embodiments, longitudinal rod 150 may project away from substantially planar lateral surfaces 14a, 14b at any intermediate angle ranging from about plus or minus 45°–0°; 35°–0°; 25°–0°; 15°–0°; and 10°–0°, for example. In at least one embodiment, longitudinal rod 150 may freely rotate within a range of about plus or minus 10°.

First receiving cavity 30 may include an arcuate rail 30a extending along a curved bottom surface of the passageway defined by receiving cavity 30. Arcuate rail 30a may be defined, at least partly, by a segment of a circle having a radius that corresponds to an external radius of the first longitudinal rod 150. For example, an outer radius of the first longitudinal rod 150 may correspond to the curved arcuate rail 30a such that first longitudinal rod 150 directly contacts arcuate rail 30a. Arcuate rail 30a may be configured to facilitate lateral pivoting of the first longitudinal rod 150 in the lateral directions as will be explained in further detail below.

First receiving cavity 30 may further include a first enlarged portion 31a and a second enlarged portion 31b. In the illustrated embodiment, first enlarged portion 31a may "fan out" laterally from arcuate rail 30a towards first lateral surface 14a and second enlarged portion 31b may "fan out" laterally from arcuate rail 30a towards second lateral surface 14b. In other embodiments, first enlarged portion 31a may "fan out" laterally and vertically from arcuate rail 30a towards first lateral surface 14a and second enlarged portion 31b may "fan out" laterally and vertically from arcuate rail 30a towards second lateral surface 14b. In some embodiments, first receiving cavity 30 may comprise a passageway with a varying radius that may be defined by at least three radii. For example, arcuate rail 30a may be defined by a first radius of curvature corresponding to the radius of a first longitudinal rod 150, an outermost edge of first enlarged portion 31a may be defined by a second radius of curvature that is larger than the radius of the first longitudinal rod 150, and an outermost edge of second enlarged portion 31b may be defined by a third radius of curvature that is larger than the radius of the first longitudinal rod 150. Additionally, the respective radii defining the outermost edge of the first and second enlarged portions 31a, 31b may be the same. In some embodiments, the cross-sectional width of first receiving cavity 30 may increase from arcuate rail 30a towards an outermost edge of first enlarged portion 31a and towards an outermost edge of second enlarged portion 31b. For example, first enlarged portion 31a and second enlarged portion 31b may fan out from arcuate rail portion 30a and be symmetrical with respect to one another. For example still, a radius of curvature of a lower surface of an internal passageway for longitudinal rod 150 may gradually increase from the arcuate rail 30a to an outermost edge of the first enlarged portion 31a and second enlarged portion 31b. Furthermore, as shown best in the top down views of FIGS. 3A-4B, the first and second enlarged portions 31a, and 31b may define the extent the first longitudinal rod 150 may be adjustably oriented. For example, the extent that first longitudinal rod 150 may be adjustably oriented laterally with respect to lateral surface 14a, 14b of connector 12.

In some embodiments, first receiving cavity 30 may include gripping elements or surfaces, such as, for example, one or more surfaces that are rough, arcuate, undulating, mesh, porous, semi-porous, dimpled and/or textured, to facilitate engagement with first longitudinal rod 150. Such features may increase a coefficient of friction or be used as an adhering surface in the use case an adhesive is additionally used, for example. As explained above, first receiving cavity 30 may define an axis A1 that extends parallel to arms 26, 28. In some embodiments, axis A1 may be disposed at alternate orientations, relative to arms 26, 28, for example, parallel, perpendicular and/or angular orientations such as acute or obtuse, coaxial and/or may be offset or staggered.

In the illustrated embodiment, first implant cavity 24 may include threaded surfaces 32 that define an opening 34 therebetween. Opening 34 may extend along an axis A1, as shown best in FIGS. 5A and 5B. Axis A1 is disposed in a substantially perpendicular orientation relative to axis A3. In some embodiments, axis A1 is disposed at alternate orientations, relative to axis A3, such as, for example, transverse and/or other angular orientations such as acute or obtuse, coaxial and/or may be offset or staggered. Opening 34 is disposed in communication with first receiving cavity 30 to facilitate fixation of first longitudinal rod 150 with connector 12.

Threaded surfaces 32 are configured for engagement with a coupling member, such as, for example, a set screw (see e.g., set screw 200 of U.S. patent application Ser. No. 16/395,498) to retain first longitudinal rod 150 within first receiving cavity 30. Example set screws may take any suitable form, type, or shape, e.g., a plain cup screw head, a knurled cup screw head, a flat screw head, an oval screw head, a cone screw head, a half-dog screw head, and a soft tipped screw head. In some embodiments, surfaces 32 may be disposed with a corresponding set screw in alternate fixation configurations, such as, for example, friction fit, pressure fit, locking protrusion/recess, locking keyway and/or adhesive. In some embodiments, all or only a portion of surfaces 32 may have alternate surface configurations to enhance engagement with a spinal rod and/or a set screw such as, for example, rough, arcuate, undulating, mesh, porous, semi-porous, dimpled and/or textured.

Threaded surfaces 32 may receive a set screw (not illustrated) that may be disposable within first implant cavity 24 between a non-locking orientation, such that first longitudinal rod 150 is translatable relative to connector 12 and a locked orientation, such that set screw 200 fixes first longitudinal rod 150 with connector 12. For example, when a set screw (not illustrated) is fully tightened the first longitudinal rod 150 may be fixed relative to the body 14 in a direction extending substantially parallel with a plane that is perpendicular with respect to Axis A1 and/or lateral surfaces 14a, 14b.

Body 14 may include a second implant cavity 44 that includes a second receiving cavity 48 that defines a passageway for a second longitudinal rod 152 (see FIG. 8). Second implant cavity 44 may include an arcuate configuration, such as, for example, a hooked shaped wall that defines a passageway that is configured to capture second longitudinal rod 152. Second implant cavity 44 may be configured to facilitate side loading of second longitudinal rod 152 with connector 12.

Second receiving cavity 48 may be configured for side loading of second longitudinal rod 152, as described herein. In some embodiments, second receiving cavity 48 may be disposed separate and apart from first receiving cavity 30. In some embodiments, second receiving cavity 48 is disposed in a side by side orientation relative to first receiving cavity 30. In some embodiments, second receiving cavity 48 is disposed in a substantially parallel orientation relative to a central axis of first receiving cavity 30 (see FIG. 5a showing Axis A3 and A4 extending parallel to one another). In other embodiments, second receiving cavity 48 may be disposed in various orientations, such as, for example, perpendicular, transverse and/or at angular orientations, such as acute or obtuse relative to first receiving cavity 30. In some embodiments, second receiving cavity 48 may be disposed offset or staggered from first receiving cavity 30.

In some embodiments, second receiving cavity 48 may have various cross section configurations, such as, for example, oval, oblong, triangular, rectangular, square, polygonal, irregular, uniform, non-uniform, variable and/or tapered. In some embodiments, surfaces of second receiving cavity 48 may include gripping elements or surfaces, such as, for example, rough, arcuate, undulating, mesh, porous, semi-porous, dimpled and/or textured to facilitate engagement with second longitudinal rod 152. Second receiving cavity 48 may define an axis A4 that extends away from lateral surfaces 14a, 14b. In some embodiments, axis A4 is disposed at alternate orientations, relative to axis A3, such as, for example, parallel, perpendicular and/or angular orientations such as acute or obtuse, coaxial and/or may be offset or staggered.

Body 14 may further include a threaded opening 40 defining an Axis A2 (see FIGS. 5A and 5B). Threaded opening 40 may be in communication with second receiving cavity 48 and configured to receive a set screw (not illustrated). Axis A2 may be disposed off-angle with respect to axis A1, e.g., in a substantially non-perpendicular orientation relative to axis A1. In some embodiments, axis A2 may be disposed at alternate orientations, relative to axis A1, such as, for example, perpendicular, transverse and/or other angular orientations such as acute or obtuse, coaxial and/or may be offset or staggered. Threaded opening 40 may be disposed in communication with second receiving cavity 48 to facilitate fixation of second longitudinal rod 152 with connector 12.

Threaded opening 40 may be configured to receive any suitable type of set screw for fixing second longitudinal rod 152 in second receiving cavity 48 relative to connector 12. For example, a plain cup screw head, a knurled cup screw head, a flat screw head, an oval screw head, a cone screw head, a half-dog screw head, and a soft tipped screw head. At least one example set screw for threaded opening 40 may be seen as set screw 202 of U.S. patent application Ser. No. 16/395,498. Installation of second longitudinal rod 152 may include tightening a second set screw (not illustrated) in threaded opening 40 such that when the second set screw (not illustrated) is fully tightened the second longitudinal rod 152 is fixed relative to the body 14. In some embodiments, longitudinal rod 152 may be fixed according to an alternate fixation configuration, such as, for example, friction fit, pressure fit, locking protrusion/recess, locking keyway and/or adhesive. In some embodiments, second receiving cavity 48 may have alternate surface configurations to enhance engagement with a spinal rod and/or a set screw such as, for example, rough, arcuate, undulating, mesh, porous, semi-porous, dimpled and/or textured.

Figure 3B:
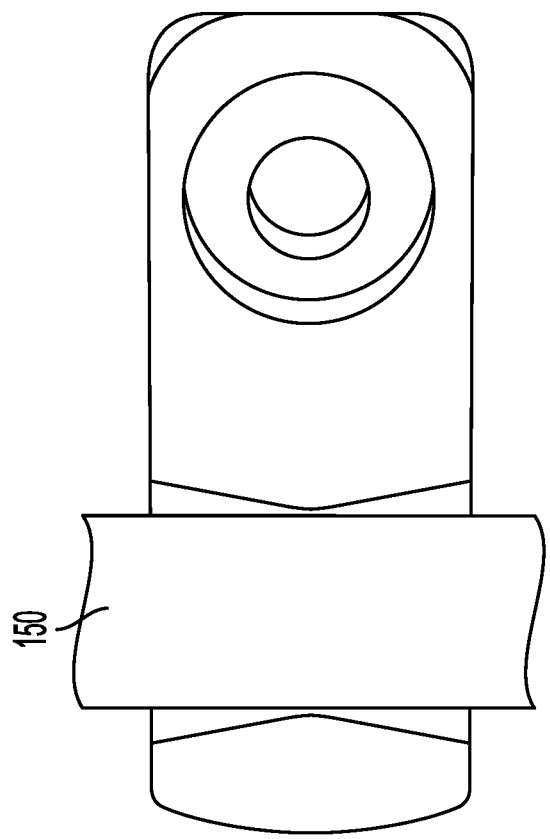
FIG. 3B is a top down view of a spinal implant connector in accordance with the principles of the present disclosure.
Figure 3A:
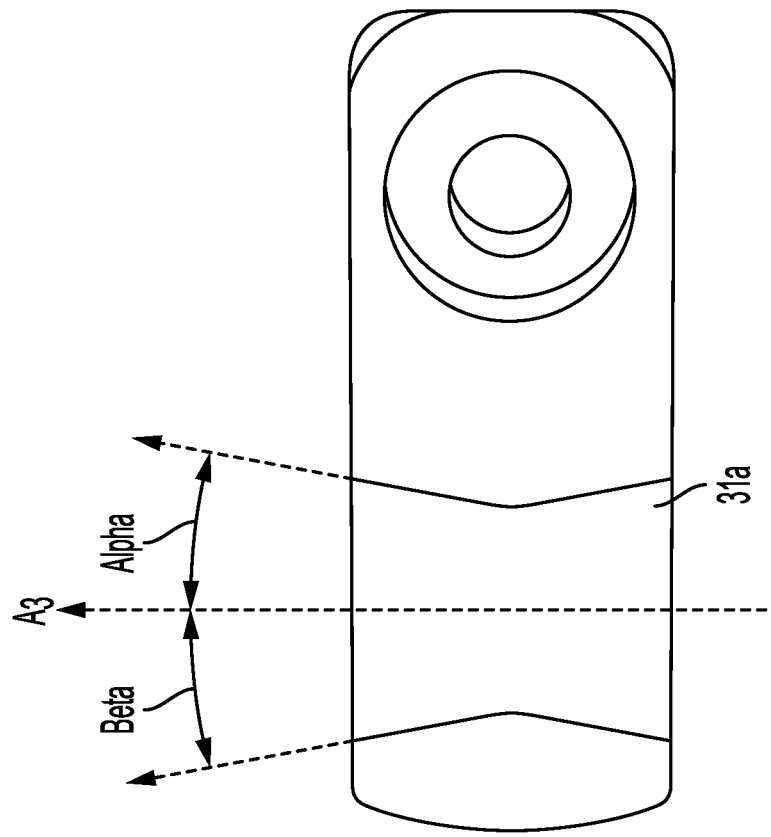
FIG. 3A is a top down view of a spinal implant connector in accordance with the principles of the present disclosure.
Figure 4B:
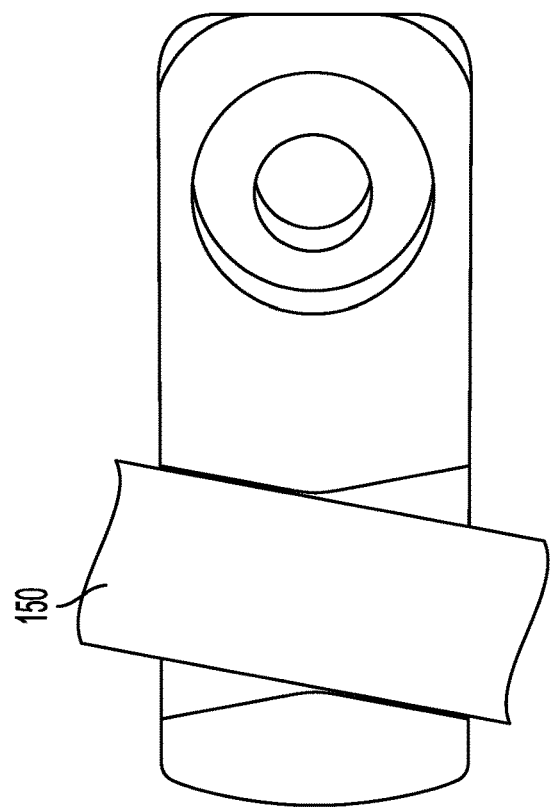
FIG. 4B is a top down view of a spinal implant connector in accordance with the principles of the present disclosure.
Figure 4A:
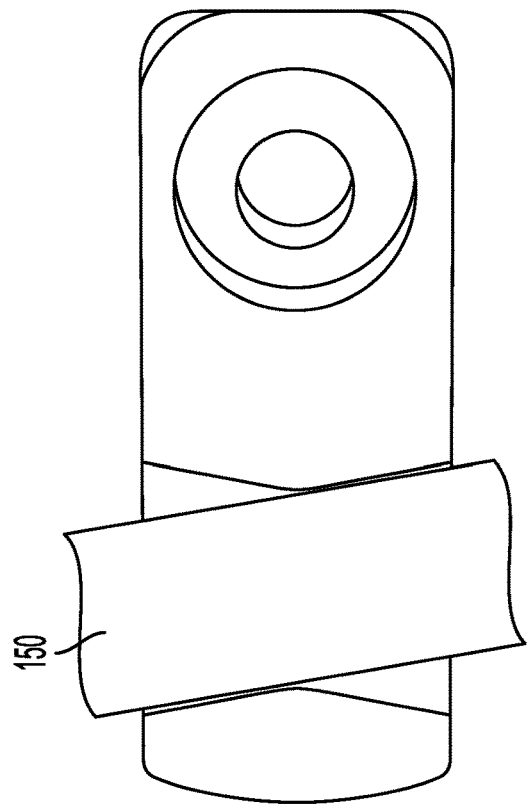
FIG. 4A is a top down view of a spinal implant connector in accordance with the principles of the present disclosure.

Referring generally to FIGS. 3A-4B, a spinal connector 12 may be illustrated with a first longitudinal rod 150. As shown in FIG. 3A, first longitudinal rod 150 may pivot laterally to the left (indicated by the symbol β) and may pivot laterally to the right (indicated by the symbol α). As shown in FIG. 3B, longitudinal rod 150 may be oriented perpendicularly with respect to lateral surfaces 14a, 14b. As shown in FIG. 4A first longitudinal rod 150 may be oriented all the way to the left such that first longitudinal rod 150 directly contacts corresponding edge portions of first and second enlarged regions 31a, 31b. For example, first longitudinal rod 150 may be oriented plus or minus 10° with respect to lateral surfaces 14a, 14b. As shown in FIG. 4B first longitudinal rod 150 may be oriented all the way to the right such that first longitudinal rod 150 directly contacts corresponding edge portions of first and second enlarged regions 31a, 31b. For example, first longitudinal rod 150 may be oriented plus or minus 10° with respect to lateral surfaces 14a, 14b. It shall be understood that first longitudinal rod 150 may pivot laterally within any suitable range determined solely be the extent of edge portions of the first and second enlarged regions 31a, 31b. In some embodiment's featuring a plurality of connectors 12 as a kit, connectors 12 may have differently sized edge portions such that each connector may pivot a different amount. In some embodiments, in addition to fixing first spinal rod 150 with a set screw, an insert may be installed in the open regions of enlarged regions 31a, 31b. For example, a shim, a wedge, a washer, an elastomeric material, a pin, an epoxy, etc. to further facilitate the fixation of first longitudinal rod 150 relative to connector 12.

Figure 6B:
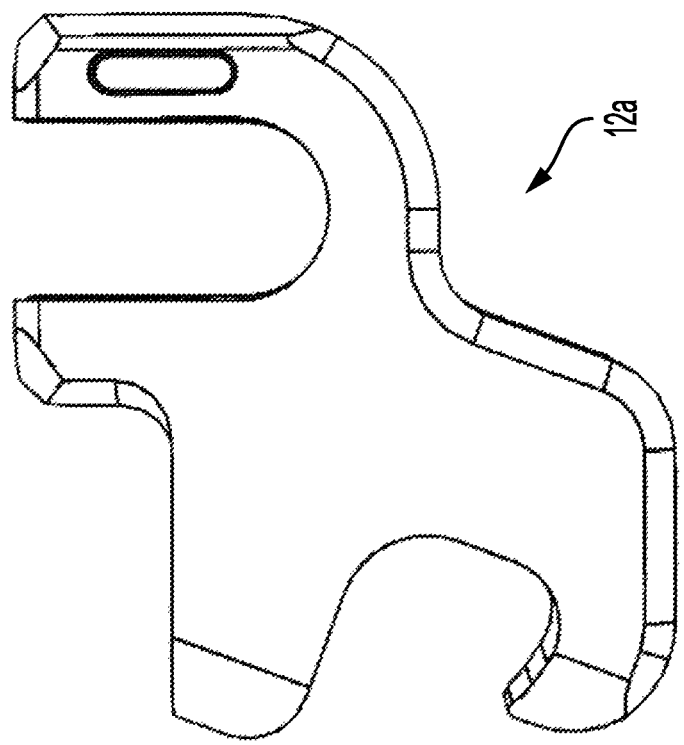
FIG. 6B is a side view of a spinal implant connector in accordance with the principles of the present disclosure.
Figure 7:
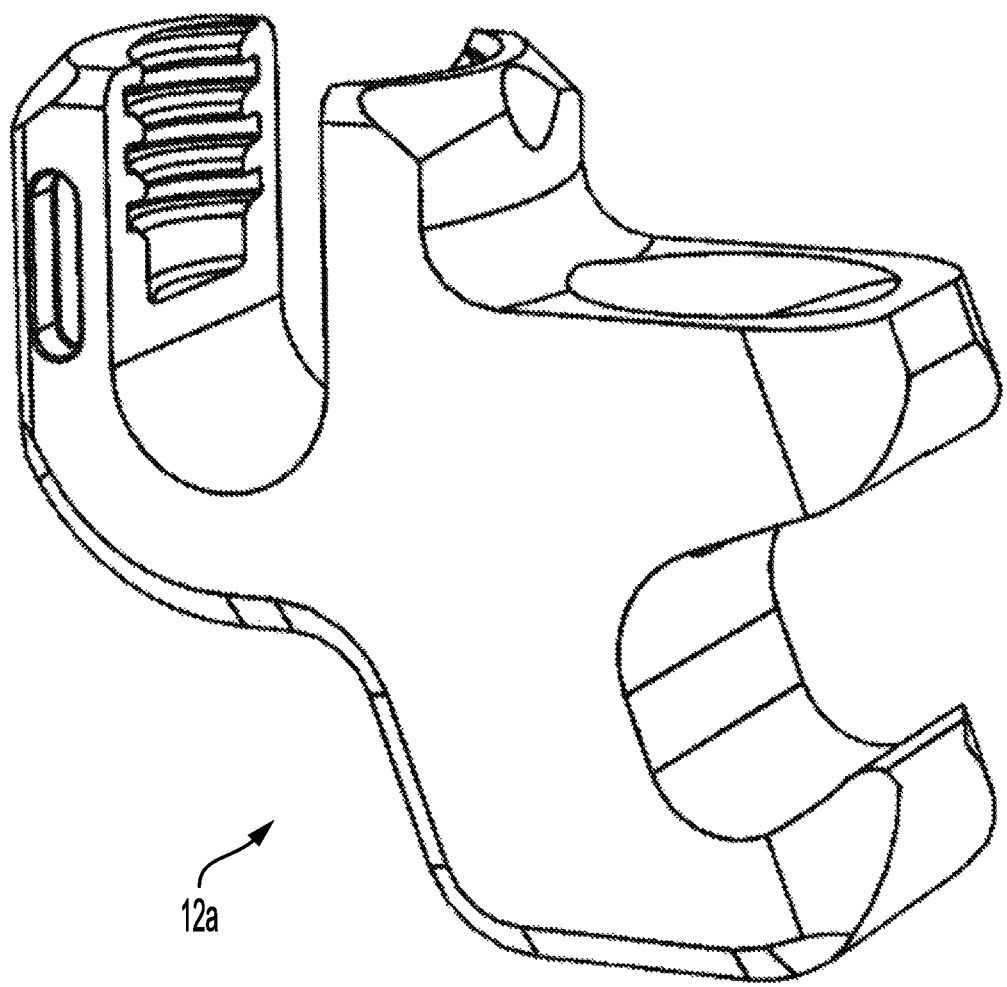
FIG. 7 is a side view of a spinal implant connector in accordance with the principles of the present disclosure.

As shown in FIGS. 6A, 6B, and 7 a similar spinal implant connector 12a is illustrated. Connector 12a may be the same as connector 12 with the exception that connector 12a may not include corresponding geometric features that enable first spinal rod 150 to pivot laterally. For example, connector 12 may not include at least one of an arcuate rail, and/or enlarged portions 31a, 31b. However, it shall be appreciated that disclosed system 10, may include a combination of connectors 12, 12a, and any other suitable connector depending on the unique circumstances of the desired spinal surgical technique.

As shown in FIG. 8, in some embodiments, spinal implant system 10 can include one or a plurality of connector(s) 12 (such as those described herein) and/or fixation elements, which may be employed with a single vertebral level or a plurality of vertebral levels. In some embodiments, connector(s) 12 may be engaged with vertebrae in various orientations, such as, for example, in series, in parallel, offset, staggered and/or alternate vertebral levels. In some embodiments, connector(s) 12 may be configured with multi-axial screws, sagittal angulation screws, pedicle screws, mono-axial screws, uni-planar screws, fixed screws, anchors, tissue penetrating screws, conventional screws, expanding screws and etc., for example. In some embodiments, connector(s) 12 may be employed with wedges, anchors, buttons, clips, snaps, friction fittings, compressive fittings, expanding rivets, staples, nails, adhesives, posts, connectors, fixation plates and/or posts, for example.

In assembly, operation and use, spinal implant system 10, may be employed with a surgical procedure, such as, for example, a correction treatment or revision treatment of an applicable condition or injury of an affected section of a spinal column and adjacent areas within a body. In some embodiments, spinal implant system 10 may be a completely or partially revised system based on a pre-existing system. In other embodiments, spinal implant system 10 may be an initially installed system, i.e., not a revision surgery technique based on a pre-existing system.

In use, to treat a selected section of vertebrae V, including vertebrae V1, V2, as shown in FIG. 8, a medical practitioner may obtain access to a surgical site including vertebrae V in any appropriate manner, such as through incision and retraction of tissues. In some embodiments, spinal implant system 10 can be used in any existing surgical method or technique including open surgery, mini-open surgery, minimally invasive surgery and percutaneous surgical implantation, whereby vertebrae V is accessed through a mini-incision, or a sleeve that provides a protected passageway to the area. Once access to the surgical site is obtained, the particular surgical procedure can be performed for treating the spine disorder.

In practice, an incision may be made in the body of a patient and a cutting instrument (not shown) may create a surgical pathway for implantation of components of spinal implant system 10. A preparation instrument (not shown) can be employed to prepare tissue surfaces of vertebrae V, as well as for aspiration and irrigation of a surgical region.

Bone screws 160 may be engaged with vertebrae V along a lateral side L of vertebrae V, as shown in FIG. 8. Bone screws 160 may be manipulated by a surgical tool to drive, torque, insert or otherwise connect bone screws 160 with vertebrae V. In some embodiments, connector 12 may be first fixedly connected to second longitudinal rod 152. Next, connector 12 may be connected to first longitudinal rod 150. At least one advantage of disclosed connector 12, is that first longitudinal rod 150 may pivot within first receiving cavity 30 and/or be oriented in a different extension direction than second longitudinal rod 152. This arrangement may provide a surgeon with significantly greater range of possibilities for installation and connection between the first longitudinal rod 150 and second longitudinal rod 152. Additionally, it should be noted that first longitudinal rod 150 and second longitudinal rod 152 may be installed in any order and/or concurrently. In at least one embodiment, second longitudinal rod 152 is installed before first longitudinal rod 150. In an alternate embodiment, first longitudinal rod 150 is installed before second longitudinal rod 152.

First longitudinal rod 150 may be disposed with bone screws 160 along vertebrae V. Connectors 12 may be disposed adjacent first longitudinal rod 150 in any suitable location. In the illustrated embodiment, each connector 12 is manipulated to dispose first longitudinal rod 150 within first receiving cavity 30 from a top loading orientation. However, as mentioned previously, in other embodiment's first longitudinal rod 150 may be alternately configured and/or received in a different loading orientation.

First longitudinal rod 150 may be fixed within first receiving cavity 30 by engaging a corresponding set screw with threads 32. The corresponding set screw may be engaged with a surgical instrument, such as, for example, a driver (not shown), which advances the corresponding set screw along axis A1 into engagement with first longitudinal rod 150 in a locking orientation. For example, a driver may engage a corresponding set screw to fix first longitudinal rod 150 with first receiving cavity 30 and for attachment of first longitudinal rod 150 with vertebrae V.

Second longitudinal rod 152 may be disposed within second receiving cavity 48 from a side loading orientation. A corresponding set screw may be disposed within threaded opening 40 and tightened along axis A2. The corresponding set screw may be engaged with a surgical instrument, such as, for example, a driver (not shown), which may advance the corresponding set screw as described herein. For example, a driver may engage the corresponding set screw to fix the second longitudinal rod 152 with connector 12 and for attachment of second longitudinal rod 152 with vertebrae V. In some embodiments, second longitudinal rod 152 may be configured to share the load applied to first longitudinal rod 150. In some embodiments, second longitudinal rod 152 may be configured to extend first longitudinal rod 150 to an adjacent vertebral level. Second longitudinal rod 152 may be configured to add support and strength to spinal implant system 10 along vertebrae V. As mentioned previously, it shall be understood that first and second longitudinal rods 150, 152 may be installed in any order. Accordingly, the discussion above with respect to first and second longitudinal rods 150, 152 is equally applicable to both rods 150, 152.

In some embodiments, spinal implant system 10 includes a second set of connectors 12, bone screws 160 and spinal rods 150, 152 (not shown) delivered along the surgical pathway to the surgical site adjacent a contra-lateral side of vertebrae V. The second set of connectors 12, bone screws 160 and spinal rods 150, 152 may be connected with the contra-lateral side of vertebrae V, similar to lateral side L described herein. In some embodiments, the spinal constructs of spinal implant system 10, as described herein, are fixed with vertebrae V in a side by side orientation and/or a bi-lateral arrangement to stabilize vertebrae V and affect growth for a correction treatment to treat spine pathologies, as described herein. In some embodiments, one or more or all of the components of spinal implant system 10 can be delivered or implanted as a pre-assembled device or can be assembled in situ, in a selected order of assembly. Additionally or alternatively, the order of assembly of the particular components of spinal implant system 10 can be varied according to practitioner preference, patient anatomy or surgical procedure parameters.

Upon completion of a surgical procedure, the above disclosed surgical instruments, assemblies and non-implanted components of spinal implant system 10 may be removed from the surgical site and the incision may be closed. One or more of the components of spinal implant system 10 can be made of radiolucent materials such as polymers, for example. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of spinal implant system 10.

In some embodiments, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the bone fasteners with vertebrae. In some embodiments, the agent may include one or a plurality of therapeutic agents and/or pharmacological agents for release, including sustained release, to treat, for example, pain, inflammation and degeneration.

It will be understood that various modifications may be made to the embodiments disclosed herein. Likewise, the above disclosed surgical installation may be performed according to an alternate sequence. Therefore, the above description should not be construed as limiting, but merely as exemplification of the various embodiments. Those skilled in the art will envision other modifications within the scope and spirit of the claims appended hereto.

What is claimed is:
1. A spinal construct comprising:
a connector including a single piece body having a first implant cavity and a second implant cavity;
the first implant cavity being defined, at least partly, by at least two threaded arm portions defining a first axis between the at least two threaded arm portions;
the first implant cavity including a first receiving cavity having an arcuate rail extending along a bottom surface and a first enlarged portion and a second enlarged portion symmetrically disposed on opposite sides of the arcuate rail, the first receiving cavity being configured to adjustably orient a first rod in a plane substantially perpendicular to the first axis and at a first height relative to the body; and
the second implant cavity including a second receiving cavity having a bottom surface configured to support a second rod at a second height relative to the body, the second implant cavity including a side opening for side loading of the second rod,
wherein the first height is higher in elevation than the second height,
wherein the threaded arm portions are configured to receive a first set screw bearing down on a top surface of the first rod such that when the first set screw is fully tightened along the first axis the first rod is fixed relative to the body in a direction extending substantially parallel with the plane,
wherein the body further includes a threaded opening communicating with the second receiving cavity, the threaded opening defining a second axis and being configured to receive a second set screw such that when the second set screw is fully tightened the second rod is fixed relative to the body, and
wherein the second implant cavity is offset from the first axis.

2. A spinal construct as recited in claim 1, wherein:
the first axis and the second axis extend in different directions, and
the first rod and the second rod extend in different directions.

3. A spinal construct as recited in claim 1, wherein:
the first axis and the second axis are disposed in a non-perpendicular orientation relative to one another, and
the first rod and the second rod extend in a non-perpendicular orientation relative to one another.

4. A spinal construct as recited in claim 1, wherein:
the arcuate rail is defined by a segment of a circle having a radius that corresponds to an external radius of the first rod, and
the arcuate rail is configured to facilitate pivoting of the first rod in the plane.

5. A spinal construct as recited in claim 1 wherein
the first and second enlarged portions define the extent the first rod may be adjustably oriented in the plane.

6. A spinal construct as recited in claim 1, wherein:
a radius of the first receiving cavity gradually increases from the arcuate rail to an outermost edge of the first enlarged portion, and
a radius of the first receiving cavity gradually increases from the arcuate rail to an outermost edge of the second enlarged portion.

7. A spinal construct as recited in claim 6, wherein:
the arcuate rail is configured to facilitate pivoting of the first rod in the plane, and
the first and second outermost edge portions define the extent the first rod may be adjustably oriented in the plane.

8. A spinal construct as recited in claim 1, wherein the first set screw comprises at least one of the following: a plain cup screw head, a knurled cup screw head, a flat screw head, an oval screw head, a cone screw head, a half-dog screw head, and a soft tipped screw head.

9. A spinal construct as recited in claim 1, wherein the first set screw and the second set screw are different types of set screws.

10. A spinal construct system comprising:
at least one anchoring member configured to couple to a corresponding pedicle screw;
a plurality of connectors, each connector including a corresponding single piece body having a corresponding first implant cavity and a corresponding second implant cavity;
each first implant cavity being defined, at least partly, by at least two corresponding threaded arm portions defining a corresponding first axis therebetween;
each first implant cavity including a corresponding first receiving cavity having an arcuate rail extending along a bottom surface and a first enlarged portion and a second enlarged portion symmetrically disposed on opposite sides of the arcuate rail, the first receiving cavity being configured to adjustably orient a first rod in a range of extension directions substantially perpendicular to the first axis and at a first height relative to the body; and
each second implant cavity including a corresponding second receiving cavity having a bottom surface configured to support a second rod at a second height relative to the body, each second implant cavity including a side opening for side loading of the second rod, wherein the first height is higher in elevation than the second height,
wherein each of the corresponding threaded arm portions are configured to receive a corresponding first set screw bearing down on a top surface of the first rod such that when the corresponding first set screw is fully tightened along the first axis the first rod is fixed relative to the corresponding body in a direction comprising the range of extension directions,
wherein each body further includes a corresponding threaded opening communicating with the corresponding second receiving cavity, each threaded opening defining a corresponding second axis and being configured to receive a corresponding second set screw such that when the corresponding second set screw is fully tightened the second rod is fixed relative to the corresponding body, and
wherein each second implant cavity is offset from the first axis of the corresponding connector.

11. The spinal construct system as recited in claim 10, wherein:
each first axis and each corresponding second axis extend in different directions, and
the first rod and the second rod extend in different directions.

12. The spinal construct system as recited in claim 10, wherein:
each first axis and each corresponding second axis are disposed in a non-perpendicular orientation relative to one another, and
the first rod and the second rod extend in a non-perpendicular orientation relative to one another.

13. The spinal construct system as recited in claim 10, wherein:
each arcuate rail is defined by a segment of a circle having a radius that corresponds to an external radius of the first rod, and
each arcuate rail is configured to facilitate pivoting of the first rod within the range of the extension directions.

14. The spinal construct system as recited in claim 10, wherein
each of the first and second enlarged portions define the extent the first rod may be adjustably oriented within the range of the extension directions.

15. The spinal construct system as recited in claim 10, wherein
a radius of each corresponding first receiving cavity gradually increases from the corresponding arcuate rail to an outermost edge of the corresponding first enlarged portion, and
wherein a radius of each corresponding first receiving cavity gradually increases from the corresponding arcuate rail to an outermost edge of the corresponding second enlarged portion.

16. The spinal construct system as recited in claim 15, wherein:
each arcuate rail is configured to facilitate pivoting of the first rod within the range of the extension directions, and
each of the first and second outermost edge portions define the extent the first rod may be adjustably oriented within the range of the extension directions.

17. The spinal construct system as recited in claim 10, wherein each first set screw comprises at least one of the following: a plain cup screw head, a knurled cup screw head, a flat screw head, an oval screw head, a cone screw head, a half-dog screw head, and a soft tipped screw head.

18. The spinal construct system as recited in claim 10, wherein each first set screw and each second set screw are different types of set screws.

\* \* \* \* \*